(12) United States Patent
Mitra et al.

(10) Patent No.: US 8,080,264 B2
(45) Date of Patent: Dec. 20, 2011

(54) NATURAL COMPOSITION FOR CURING HEPATITIS-B, METHODS FOR MAKING THE SAME AND PHARMACEUTICAL FORMULATIONS THEREOF

(75) Inventors: Shankar Kumar Mitra, Bangalore (IN);
Ekta Saxena, Bangalore (IN);
Mallikarjun N. Dixit, Bangalore (IN)

(73) Assignee: Himalaya Global Holdings Ltd., Dubai (IN)

( * ) Notice: Subject to any disclaimer, the term of this patent is extended or adjusted under 35 U.S.C. 154(b) by 0 days.

(21) Appl. No.: 12/820,064

(22) Filed: Jun. 21, 2010

(65) Prior Publication Data

US 2010/0260875 A1    Oct. 14, 2010

Related U.S. Application Data

(62) Division of application No. 11/056,420, filed on Feb. 11, 2005, now abandoned.

(30) Foreign Application Priority Data

Nov. 24, 2004  (IN) .......................... 2354/DEL/2004

(51) Int. Cl.
*A61K 36/00* (2006.01)
(52) U.S. Cl. ........................................ 424/725
(58) Field of Classification Search .................. None
See application file for complete search history.

(56) References Cited

U.S. PATENT DOCUMENTS

| | | | |
|---|---|---|---|
| 4,908,207 A | | 3/1990 | Hakky et al. |
| 5,112,604 A | * | 5/1992 | Beaurline et al. ............. 424/490 |
| 5,648,089 A | | 7/1997 | Shawkat et al. |
| 5,939,072 A | | 8/1999 | Zhou et al. |
| 5,948,438 A | * | 9/1999 | Staniforth et al. ............ 424/464 |
| 6,136,316 A | | 10/2000 | Mehrotra et al. |
| 6,214,350 B1 | | 4/2001 | Hwang et al. |
| 6,426,098 B1 | | 7/2002 | Yang |
| 6,428,819 B1 | | 8/2002 | Lavie et al. |
| 6,589,570 B1 | | 7/2003 | Thyagarajan et al. |
| 6,790,837 B2 | * | 9/2004 | Heimbecher et al. ........... 514/43 |
| 7,198,804 B2 | | 4/2007 | Cho et al. |
| 2003/0104050 A1 | * | 6/2003 | Matharu et al. ............... 424/465 |

FOREIGN PATENT DOCUMENTS

| | | | |
|---|---|---|---|
| CN | 1112834 A | * | 12/1995 |
| CN | 1233477 A | * | 11/1999 |
| JP | 06016516 A | | 1/1994 |
| JP | 2001/192317 A | | 7/2001 |
| JP | 2003-048844 A | | 2/2003 |
| JP | 2003/137726 A | | 5/2003 |

OTHER PUBLICATIONS

"Forever Musta: *Cyperus rotundus*". [Retrieved from the internet on Apr. 8, 2011]. Retrieved from the Internet: <URL: http://bestmusta.com/aboutbestmusta.html>.*

Avert: Averting HIV and AIDS. "Hepatitis A, Hepatitis B & Heptaitis C". [Retrieved from the Internet on Mar. 5, 2009] Retrieved from: <http://www.avert.org/hepatitis.htm>.*

Kubic, M. U.S. Food and Drug Administration: New Ways to Prevent and Treat AIDS. 1997 FDA Consumer. Published- May 1997 and revised Jan. 1998 [Retrieved from the Internet: Oct. 15, 2008]. Retrieved from: >http://www.rda.gov/FDAC/features/1997/197_aids.html>.*

EFSA: European Food Safety Authority "EFSA advises on the safety of paraben usage in food", Press release (Sep. 29, 2004). [Retrieved from the Internet on Mar. 5, 2009] Retrieved from: <http://www.efsa.europa.eu/EFSA/efsa_locale-1178620753812_1178620781222.htm>.*

Bhattacharya, A.K. et al., A preliminary study on the safety and efficacy of HD-03/ES therapy in patients with chronic hepatitis B: a prospective clinical study, Journal of Herbal Medicine and Toxicology, 2009, vol. 3, Issue 2, pp. 137-141.

Kar, Premashis et al., HD-03/ES: A promising herbal drug for HBV antiviral therapy, Antiviral Research, 2009, vol. 84, pp. 249-253.

Chin R. et al., New Therapies for the Treatment of Chronic Hepatitis B Infection, Curr Opin Infect Dis, vol. 11, No. 6, Dec. 1998, pp. 719-726, PubMed Abstract.

Hepatitis A, Hepatitis B & Hepatitis C, Avert.org: Averting HIV and AIDS (Retrieved from <http://www.avert.org/hepatitis.htm> on Mar. 5, 2009.

Kubic, M., U.S. Food and Drug Administration: New Ways to Prevent and Treat AIDS, 1997 FDA Consumer (Retrieved from <http://www.fda.gov/FDAC/features/1997/197_aids.html> on Oct. 15, 2008, May 1997.

About the Plant List 2010 retrieved from "http://www.theplantlist.org/about".

Synonyms of *Cyperus scariosus*, The Plant List 2010 retrieved from http://www.theplantlist.org/tpl/record/kew-238443.

Synonyms of *Cyperus rotundus*, The Plant List 2010 retrieved from http://www.theplantlistorg/tpl/record/kew-238342.

* cited by examiner

*Primary Examiner* — Amy L Clark
(74) *Attorney, Agent, or Firm* — Knobbe, Martens, Olson & Bear, LLP

(57) ABSTRACT

Disclosed herein is a natural antiviral composition comprising extracts of plant *Cyperus rotundus* and/or plant *Cyperus scariosus* and a pharmaceutically acceptable carrier. Also disclosed are methods of making the plant extract, methods for preparing the composition and methods of treating diseases related to acute and chronic hepatitis B and other viral diseases of the liver.

16 Claims, 5 Drawing Sheets

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: chemically synthesized primer

<400> SEQUENCE: 1
ctgtggagtt actctcgttt ttgc                                        24

<210> SEQ ID NO 2
<211> LENGTH: 24
<212> TYPE: DNA
<213> ORGANISM: Artificial Sequence
<220> FEATURE:
<223> OTHER INFORMATION: chemically synthesized primer

<400> SEQUENCE: 2
ctaacattga gattcccgag attg                                        24

<210> SEQ ID NO 3
<211> LENGTH: 17
<212> TYPE: DNA
<213> ORGANISM: Artificial Sequence
<220> FEATURE:
<223> OTHER INFORMATION: chemically synthesized primer

```
<400> SEQUENCE: 3
gaatctgatt tccaata                                              17

<210> SEQ ID NO 4
<211> LENGTH: 17
<212> TYPE: DNA
<213> ORGANISM: Artificial Sequence
<220> FEATURE:
<223> OTHER INFORMATION: chemically synthesized primer

<400> SEQUENCE: 4
acgggtctac tatttta                                              17
```

US 8,080,264 B2

NATURAL COMPOSITION FOR CURING HEPATITIS-B, METHODS FOR MAKING THE SAME AND PHARMACEUTICAL FORMULATIONS THEREOF

FIELD OF THE INVENTION

This invention, in general, relates to a herbal antiviral composition capable of curing hepatitis-B and other related viral diseases. More particularly, the present invention provides for a herbal composition comprising extract of plant *Cyperus rotundus* and/or plant *Cyperus scariosus* and a pharmaceutically acceptable carrier, methods of making the same, pharmaceutical formulations thereof and methods of treating acute and chronic hepatitis, hepato-cellular carcinomas and liver disorders due to infection by Hepatitis-B Virus (HBV) in humans using said natural herbal medicament.

BACKGROUND OF THE INVENTION

"Hepatitis" means "inflammation of the liver" and can be caused by a virus called Hepatitis B and more recently other subtypes C, D, E, F and G are reported to cause human hepatitis. Other types of infection (bacteria, fungal and TB), toxic drugs, poisons, alcoholism, vascular disorders and immune system diseases also cause hepatitis in humans.

It is estimated that 350 million people are infected with hepatitis-B virus worldwide. Around 50 million cases diagnosed annually. The carrier rate is as high as 20% in people from Asia and Africa. Hepatitis B is usually transmitted through blood transfusion, sexual contact, and saliva. It can be transmitted from infected mothers to newborn infants and become persistent HBV carriers. A chronic HBV infection can be entirely benign with normal liver blood tests (chronic carrier state) or may be an aggressive inflammation process that can lead to severe cirrhosis. The risk of liver cancer (hepatoma) is high in cirrhosis caused by HBV.

In the recent years, chemotherapy for hepatits and other liver disorders has witnessed tremendous activity and resulted into two FDA approved treatments for hepatitis B. The first drug Intron A (interferon alfa-2b) gives 20% lasting response in treated patients. A new drug, Lamivudine is under intense investigation with respect to its role in the management of Hepatitis B. According to Dienstag et al., Lamivudine mono therapy in hepatitis patients for one year had shown positive effect with respect to histology, virulence and biochemical features. Other drugs, which are under development, are Peginterferon alfa-2a (Pegasys), Emtricitabine and Zadaxin (thymosin-alpha) etc.

There are many herbal compositions that have been developed for hepatoprotective and acute hepatitis diseases that comprises *Andrographis paniculata, Phyllanthus amarus, Phyllanthus niruri, Eclipta alba, Salvia miltiorrhiza, Panax ginseng*, Licorice Root, *Piccrorhiza kurroa, Tinospora cordifolia* and *Cichorium intybus* etc.

To overcome the challenges posed by hepatitis B and other subtype viral infections, major research activities have been directed at developing new pharmaceutical formulations, which are in turn aimed at developing a formulation to have antiviral property, anti HbsAg activity, hepatoprotective activity and immunomodulating activity. The recent research is also aimed at safe and effective treatments for Hepatitis B virus infections, hepato cellular carcinoma, and hepatoprotective and immunomodulation activities.

RELATED ART

U.S. Pat. No. 6,589,570 to Thyagarajan et al. discloses a pharmaceutical formulation useful for the treatment of hepatitis B, hepatitis C and other viral infections of the liver and a process for its preparation U.S. Pat. No. 6,428,819 to Lavie et al. discloses the preparation of a pharmaceutical composition comprising *Hypericum perforatum* extracts for the treatment of hepatitis.

U.S. Pat. No. 6,426,098 to Yang et al. discloses Herbal composition for hepatic disorders comprising *Salvia miltiorrhiza* and *Polyporus umbellatus*.

U.S. Pat. No. 6,214,350 to Hwang et al. teaches the process for preparing an anti-viral medicinal product from chinese herbal medicines.

U.S. Pat. No. 6,136,316 to Mehrotra et al. discloses a novel polyherbal composition for hepatoprotective activity and composition for treatment of conditions related to hepatitis B and E infection.

U.S. Pat. No. 5,939,072 to Zhou et al. discloses the composition that includes polysaccharides derived from mushroom viz. Maitake, Shiitake, Reishi, Poria, Cordyceps and Hericium for the treatment of viral infections of the liver.

U.S. Pat. No. 5,648,089 to Shawkat et al teaches the preparation of herbal mixture includes Ecballium elaterium in the form of nasal drops for the treatment of hepatitis.

U.S. Pat. No. 4,908,207 to Hakky et al discloses a herbal composition comprising *Cyperus rotundus* for the treatment of compromised immunodeficiency in humans.

SUMMARY OF THE INVENTION

It is the principal aspect of the present invention to provide for the hepatoprotective and immunomodulatory effects of the extracts of plant *Cyperus rotundus, Cyperus scariosus* alone or in combination thereof.

In another aspect, the present invention discloses the efficacy of the extracts of plants *Cyperus rotundus* and/or *Cyperus scariosus* against hepatitis B virus.

In one another aspect, the present invention discloses the efficacy of the extracts of plants *Cyperus rotundus* and/or *Cyperus scariosus* against HIV virus.

In still another aspect, the present invention provides for a pharmaceutical composition comprising herbal extract with pharmaceutically acceptable carrier wherein the herbal extract is prepared from the herbal plants *Cyperus rotundus* and/or *Cyperus scariosus*.

In yet another aspect, the present invention provides for a pharmaceutical composition containing a therapeutically effective amount of extracts of plants *Cyperus rotundus* and/or *Cyperus scariosus* or a pharmaceutical composition comprising said extract of said plants, in a pharmaceutically acceptable carrier or otherwise.

In one another aspect, the present invention provides for determining the role of a therapeutically effective amount of extracts of plants *Cyperus rotundus* and/or *Cyperus scariosus* in clearance of HBsAg in circulation and suppression of HBsAg production.

In still another aspect, the present invention provides for determining the role of a therapeutically effective amount of extracts of plants *Cyperus rotundus* and *Cyperus scariosus* in inhibiting HBV-DNA polymerase enzyme which is required for the replication for the virus, thus acting as antiviral preventing the multiplication of virus itself In yet another aspect, the present invention provides for determining the role of a therapeutically effective amount of extracts of plants *Cyperus rotundus* and *Cyperus scariosus* in inhibiting Reverse Transcriptase enzyme, which is required for the initiation of HBV replication.

In still yet another aspect, the present invention provides for determining the role of a therapeutically effective amount of extracts of plants *Cyperus rotundus* and *Cyperus scariosus* as hepatoprotective and anti hepatotoxic properties against the liver cell toxicity by hepatitis virus and other hepatotoxic agents.

In yet another aspect, the present invention provides for determining the role of a therapeutically effective amount of extracts of plants *Cyperus rotundus* and/or *Cyperus scariosus* as immunomodulator to potentiate the immune system of HBV infected patients towards viral clearance and protective antibody (anti HBs) responses.

In yet another aspect, the present invention discloses methods of treating hepatitis B patients using a medicament comprising therapeutically effective amount of extracts of plants *Cyperus rotundus* and/or *Cyperus scariosus* with pharmaceutically acceptable carrier.

It is also an aspect of the present invention to develop a method of treating liver disorders including liver cirrhosis, hepato-cellular carcinomas.

In one another aspect, the present invention discloses methods of producing extracts from plant *Cyperus rotundus* and/or *Cyperus scariosus*.

In one preferred embodiment, there is provided a natural hepatitis B antiviral composition comprising a therapeutically effective amount of the extract of plant *Cyperus rotundus* and/or *Cyperus scariosus*, wherein the extract is prepared by all parts of said herb *Cyperus rotundus* and preferably its rhizomes/roots.

In another preferred embodiment, there is provided a natural hepatitis B antiviral composition comprising a therapeutically effective amount of the extract of plants, *Cyperus rotundus* and/or *Cyperus scariosus*, wherein the extract is prepared by all parts of said herb *Cyperus scariosus* and preferably its rhizomes/roots.

In one another preferred embodiment, there is provided a natural hepatitis B antiviral composition comprising methanolic extract of rhizomes/roots of plant *Cyperus rotundus*.

In one another preferred embodiment, there is provided a natural hepatitis B antiviral composition comprising methanolic extract of rhizomes/roots of plant *Cyperus* scariosus.

In still another preferred embodiment, there is provided a natural hepatitis B antiviral composition comprising an equi molar mixture of methanolic extract of rhizomes/roots of plant *Cyperus rotundus* and rhizomes/roots of *Cyperus scariosus*.

In another preferred embodiment, there is provided a method of extraction of plant materials *Cyperus rotundus* and/or *Cyperus scariosus* with organic solvents for example n-hexane, chloroform, ethyl acetate, acetone, alcohol, methanol and water etc.

In yet another preferred embodiment, there is provided a method of screening crude extracts of plant material *Cyperus rotundus* and *Cyperus scariosus* for HbsAg suppression and methanol extract of *Cyperus rotundus* being most active with 94.19% of suppression activity followed by alcohol extract of *Cyperus rotundus* with 90% suppression activity.

In still another preferred embodiment, there is provided a detailed study of chemical and biological efficacy of methanol extract of *Cyperus rotundus* in Hepatitis B viral infections and other liver disorders.

In one another preferred embodiment, there is provided a method of obtaining the active fraction of methanol extract of plant *Cyperus rotundus* by subjecting the extract to bioassay-guided fractionation employing hexane soluble fraction (J-1), dichloromethane soluble fraction (J-2), ethyl acetate soluble fraction (J-3), methanol soluble fraction (J-4) and water-soluble fraction (J-5).

In yet another preferred embodiment, there is provided a screening of bioassay guided fractions and ethyl acetate soluble fraction (J-3) being most active with 98% of HbsAg suppression followed by methanol soluble fraction (J-4) with 64% of suppression.

In still yet another preferred embodiment, there is provided a method of purifying the active fraction (J-3) by column chromatography over silicagel with gradient elution of dichloromethane, ethylacetate and methanol resulting into two most active purified fractions eluted with 25% ethyl acetate in dichloromethane fraction (J-8) with 84% suppression activity and 50% ethyl acetate in dichloromethane fraction (J-9) being the most as 98% suppression activity.

In yet another preferred embodiment, there is provided a natural antiviral composition for use in the treatment of Hepatitis B virus comprising a therapeutically effective amount of extracts of plant *Cyperus rotundus* comprising Alkaloids, Bitters, Glycosidic compounds, Tannins, Fixed oils, Procyanidins, Anthraquinone glycosides, Flavonoids, Terpenoids, Terpenoid glycosides and amino acids as active constituents.

In yet another preferred embodiment, there is provided a natural antiviral composition for use in the treatment Hepatitis B virus comprising a therapeutically effective amount of extracts of plant *Cyperus scariosus* comprising Alkaloids, Bitters, Glycosidic compounds, Tannins, Fixed oils, Procyanidins, Anthraquinone glycosides, Flavonoids, Terpenoids, Terpenoid glycosides and amino acids as active constituents.

In yet another preferred embodiment, there is provided a natural antiviral composition against Hepatitis B virus containing a therapeutically effective amount of extracts of plants *Cyperus rotundus* and/or *Cyperus scariosus* in a pharmaceutically acceptable carrier wherein the composition is in an oral dosage form.

In another preferred embodiment, there is provided a natural antiviral composition against Hepatitis B virus comprising making syrup containing a therapeutically effective amount of extracts of plants *Cyperus rotundus* and/or *Cyperus scariosus* in an amount of 50 mg to 500 mg and pharmaceutically acceptable carriers comprising Sugar D 30 (3.4 to 3.75 gm), Citric acid (0.01 to 0.02 mg), Methyl paraben sodium (0.01 mg), Propyl paraben sodium (0.0025 mg), Strawberry flavor (0.005 mg) and DM Water (Qs) per 5 ml of dosage form.

In yet another preferred embodiment, there is provided a natural antiviral composition against Hepatitis B virus comprising making granules containing a therapeutically effective amount of extracts of plants *Cyperus rotundus* and/or *Cyperus scariosus* in an amount of 50 to 500 mg and pharmaceutically acceptable carriers comprising Microcrystalline cellulose (100 to 450 mg), P.G. Starch (about 50 mg), Lactose (50 to 300 mg), Dibasic calcium phosphate (50 to 250 mg), DM Water (Qs) per 300 to 900 mg of dosage form.

In another preferred embodiment, there is provided a natural pharmaceutical composition comprising granules (500 to 900 mg) as per paragraph [0047] and pharmaceutically acceptable excipients comprising Sodium starch glycolate (about 30 mg), Calcium carbonate (about 14 mg), Cabosil M5 (about 3 mg) and Magnesium stearate (about 3 mg) for further compression to obtain tablets.

In another preferred embodiment, there is provided a natural pharmaceutical composition comprising granules (300 to 500 mg) as per paragraph [0047] and pharmaceutically acceptable excipients comprising Cabosil M5 (about 2 mg) and Magnesium stearate (about 3 mg) for further filling in capsules.

In one another preferred embodiment, there is provided a delivery system containing natural antiviral composition against Hepatitis B virus wherein the delivery system comprises tablets, capsules, pills, granules and syrups, powders, concentrates, dry syrups etc.

In yet another preferred embodiment, there is provided a natural antiviral composition against Hepatitis B virus comprising a potency equivalent of the extract ranging from about 5 mg to about 2000 mg.

In still a preferred embodiment, there is provided a method of treating Hepatitis by administering to a patient a natural antiviral composition comprising a therapeutically effective amount of extracts of plants *Cyperus rotundus* and/or *Cyperus scariosus* in a pharmaceutically acceptable carrier or otherwise.

In still another preferred embodiment, there is provided a natural antiviral composition, wherein the composition is used for inhibiting cell growth, suppression of production of HbsAg, inhibition of reverse transcriptase enzyme, destabilization of viral RNA in the cell, stimulation of the immune system by the way of macrophage activation, proinflammatory cytokine production and Nitric oxide production and reverse oxidative damage by TBH and complete protection to the hepatocytes.

In still another preferred embodiment, there is provided a process for obtaining a natural antiviral composition against Hepatitis B virus, the process comprising extracting *Cyperus rotundus* rhizomes by percolation, filtering the plant extract, concentrating the plant extract to dryness on rotatory evaporator or on steam bath at optimum temperature and producing a herbal composition comprising the said dry extract and pharmaceutically acceptable carrier.

In still another preferred embodiment of the present invention, there is provided a process for preparation of a novel herbal composition. The method comprising, extracting plant extract from *Cyperus rotundus* rhizomes by hot soxhalation, filtering the plant extract, concentrating the plant extract to dryness on rotatory evaporator or on steam bath at optimum temperature and producing a herbal composition employing the said dry extract and pharmaceutically acceptable carrier.

In still another preferred embodiment of the present invention, there is provided a process for preparation of a novel herbal composition. The method comprising extracting plant extract from *Cyperus scariosus* rhizomes by percolation, filtering the plant extract, concentrating the plant extract to dryness on rotatory evaporator or on steam bath at optimum temperature and producing a herbal composition employing the said dry extract and pharmaceutically acceptable carrier.

In still another preferred embodiment of the present invention, there is provided a process for preparation of a novel herbal composition. The method comprising extracting plant extract from *Cyperus scariosus* by hot soxhalation, filtering the plant extract, concentrating the plant extract to dryness on rotatory evaporator or on steam bath at optimum temperature and producing a herbal composition employing the said dry extract and pharmaceutically acceptable carrier.

BRIEF DESCRIPTION OF THE DRAWINGS

Further objects of the present invention together with additional features contributing thereto and advantages accruing there from will be apparent from the description of preferred embodiments of the present invention which are shown in the accompanying drawing figures.

Lane 1 control shows amplification of 523 bp;

Lane 2 shows partial elimination following 6 days of incubation with Cy 23;

Lane 3 marker; and

Lane 4 shows complete elimination viral DNA fragment (no amplification) following 12 days of incubation with Cy 23

Figure 2:
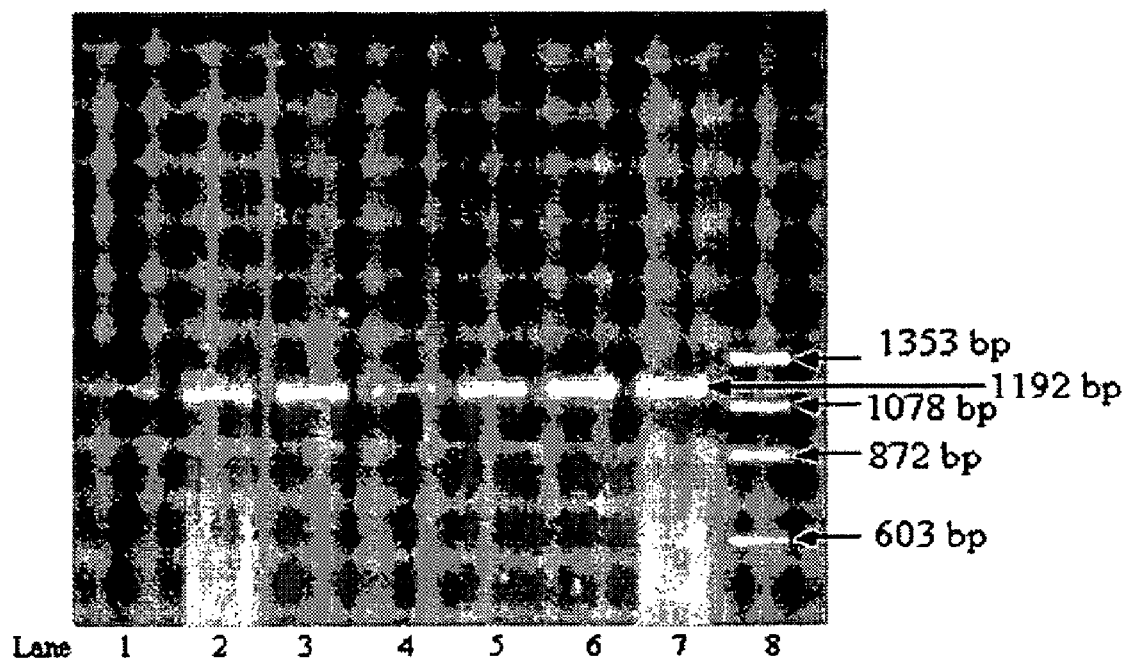

FIG. 2 PCR of restrict digested DNA samples from Liver tissues of wild ducks run on 2% agarose gel, Lane 1-7: Clinical samples (Liver) showing amplification of 1192 by ccc DNA specific to duck hepatitis B virus;

Lane 8: DNA marker-Phi. X 174 DNA-Hind III Digest

Figure 3:
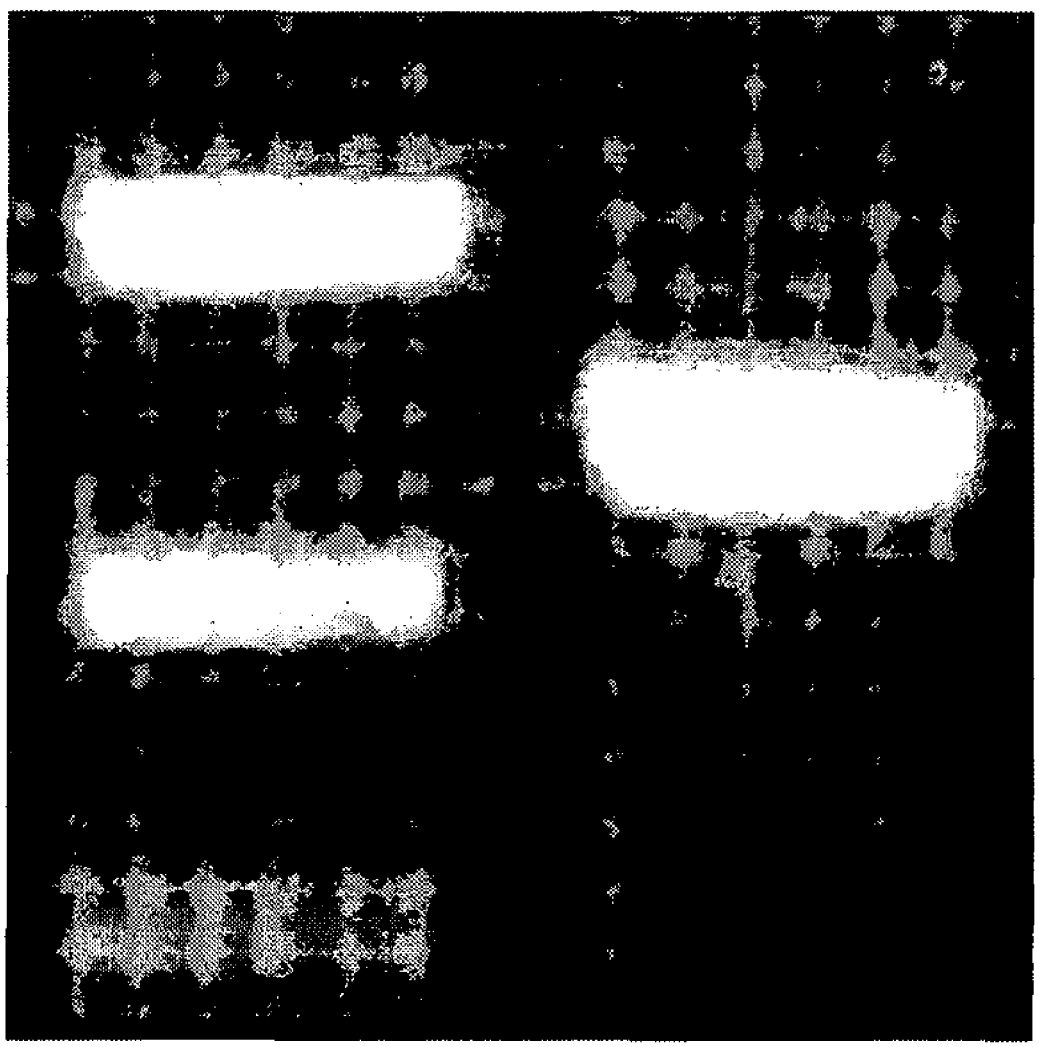

FIG. 3 Agarose gel showing PCR amplification 1192 by fragment of cccDNA specific to DHBV (lane 2).

Figure 4:
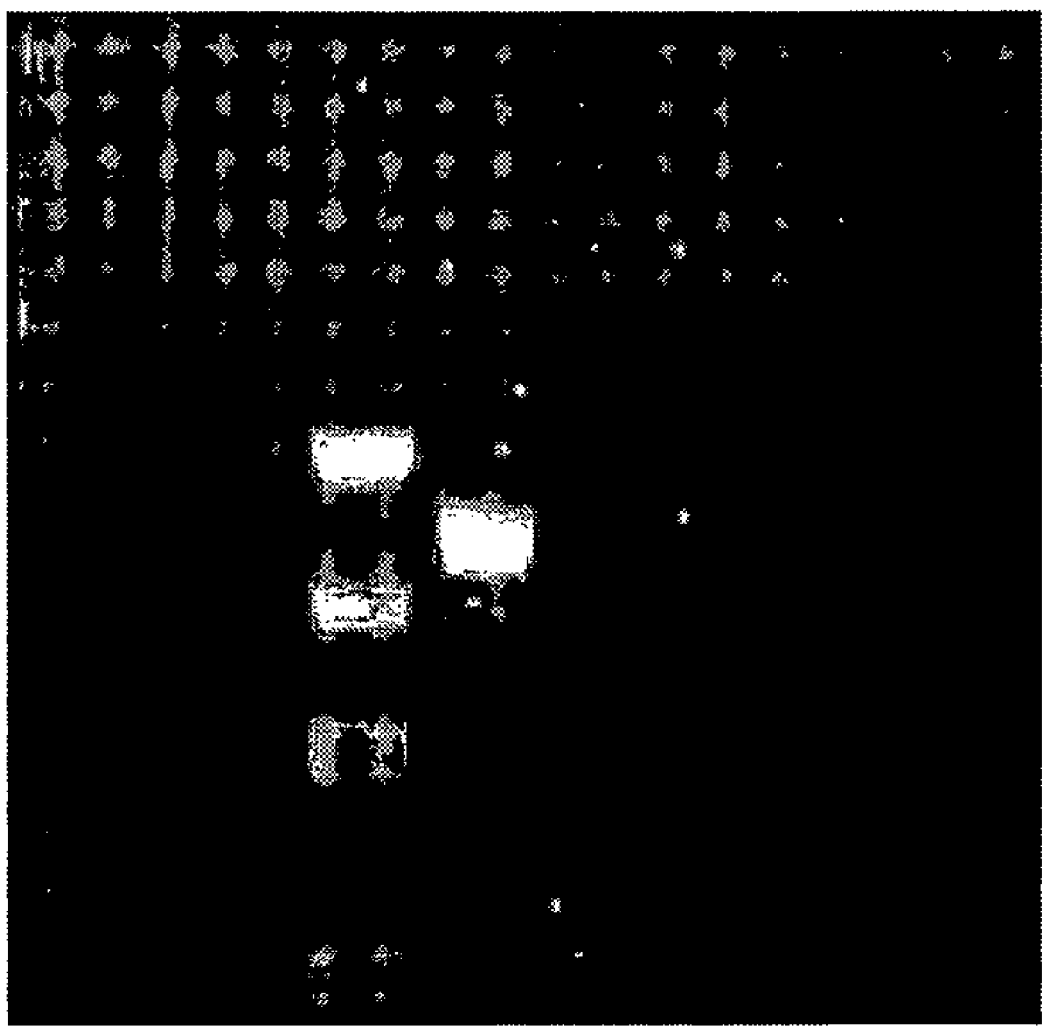

FIG. 4 Agarose gel showing PCR amplification 1192 by fragment of cccDNA specific to DHBV (lane 2) against DHBV negative samples, which do not show any amplification (Lane 3, 4 and 5).

Figure 5:
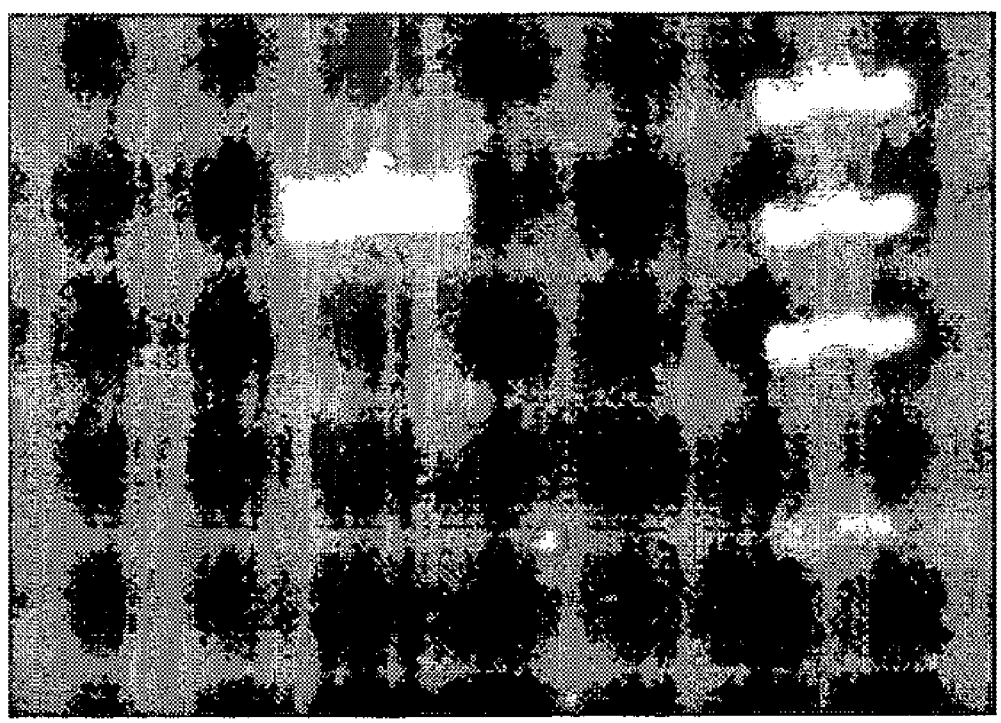

FIG. 5 Agarose gel showing PCR amplification 1192 by fragment of cccDNA specific to DHBV (lane 2) in the positive control group where as no amplification was seen in lane 1 (Normal Control) and Lane 3 (Cy 23 treated). Lane 4 is the DNA marker.

DETAILED DESCRIPTION OF THE INVENTION

The present invention involves the selection and identification of the herbs and obtaining the extract by subjecting the same to solvent extraction. The bioassay guided fractionation of the extract to identify the active markers or active fraction and to develop effective and safe composition for the use in human beings and animals in Hepatitis B and all kinds of liver disorders and hepato carcinoma patients.

*Cyperus rotundus* Linn a pestiferous perennial weed with dark green glabrous culms, 0.5-2 ft. high, arises from a system of underground tubers. It is found throughout India up to an elevation of 6,000 ft. The plant has an elaborate underground system consisting of tubers, rhizomes and roots. The tubers are white and succulent when young, and hard and black when mature. (Nambiyar, Madras agric. J., 1944, 32, 47). The tubers of the plant have an aromatic odour. It is reported to contain mainly terpenoids along with few saponins and alkaloids. Around 20 sesquiterpenoids have been isolated from *C. rotundus*. (Biol. Pharma. Bull. 25(1), 128-30 (2002).

The tubers are said to be diaphoretic and astringent, and in indigenous medicine they are given for disorders of the stomach and irritation of the bowels. The roots have been reported for emmenagogue, sedative, antispasmodic, demulcent and hemostatic and uterine disorders. It is tonic, stomachic, expectorant, diuretic, antifibrile, decongestant and antirheumatic. (Wealth of India, Raw Materials, Vol. II, C.S.I.R., Delhi, 1950.) The root extract of *C. rotundus* possess tranquilizing activity and it had also shown smooth muscle relaxant activity on rabbit ileum. It also showed significant antipyretic and antiinflammatory activities. (Indian J. Med. Res. 1970, 58, 103).

*Cyperus scariosus* delicate, slender sedge, met with in damp places in Bengal, Uttar Pradesh and eastern and southern parts of India. The plant produces deep brown tubers with aromatic odour, which are used for the same purposes as the tubers of *C. rotundus*. The tubers are used in perfumery. They are tonic, stomachic and are considered stimulant for the heart (Caius, J. Bombay nat. Hist. Soc., 1935.38167).

EXAMPLE 1

Preparation of Extract from *Cyperus rotundus* by Percolation Method

The shade dried material of tubers/rhizomes/roots of *Cyperus rotundus* was pulverized to coarse powder and about 1 Kg each of powdered material placed in different flasks and extracted with n-hexane, dichloromethane, chloroform, ethyl acetate, acetone, ethanol, methanol, water, chloroform and methanol (1:1), methanol and water (1:1) and ethyl alcohol and water (1:1) at room temperature for 24 h to 48 h., then plant extracts were filtered and concentrated to dryness on rotatory evaporator or on steam bath at optimum temperature and under reduced pressure.

EXAMPLE 2

Preparation of Extract from *Cyperus rotundus* by Hot-Soxlation Method

The coarse powdered material of tubers/roots/rhizomes of *Cyperus rotundus* was subjected to hot-soxlation using solvents n-hexane, dichloromethane, chloroform, ethyl acetate, acetone, ethanol, methanol, water, chloroform and methanol (1:1), methanol and water (1:1) and ethyl alcohol and water (1:1) at optimum temperature and recycled until extraction is completed, then plant extracts were filtered and concentrated to dryness on rotatory evaporator or on steam bath at optimum temperature.

All extracts such as n-hexane extract (CR-1), dichloromethane extract (CR-2), chloroform extract (CR-3), ethyl acetate extract (CR-4), acetone extract (CR-5), ethanol extract (CR-6), methanol extract (CR-7), water extract (CR-8), choloroform:methanol (1:1) extract (CR-9), methanol:water (1:1) extract (CR-10) and ethanol: water (1:1) extract (CR-11) prepared from the tubers/rhizomes/roots of *Cyperus rotundus* by using percolation method or hot-soxlation method were subjected to HPTLC (High Performance Thin Layer Chromatography) and HPLC (High performance Liquid chromatography) in various mobile phases on precoated TLC plates (Merck) and ODS column for qualitative and quantitative estimation of marker compounds and active principles. It was found that the extracts CR-1 to CR-11 were qualitatively and quantitatively similar to each other.

EXAMPLE 3

Preparation of Extract from *Cyperus scariosus* by Percolation Method

The shade dried material of tubers/rhizomes/roots of *Cyperus scariosus* were pulverized to coarse powder and about 1 Kg of powdered material was placed in different flasks and extracted with n-hexane, dichloromethane, chloroform, ethyl acetate, acetone, ethanol, methanol, water, chloroform and methanol (1:1), methanol and water (1:1) and ethanol and water (1:1) at room temperature for 24 h to 48 h, then plant extract were filtered and concentrated the filtered plant extract to dryness on rotatory evaporator or on steam bath at optimum temperature and under reduced pressure.

EXAMPLE 4

Preparation of Extract from *Cyperus scariosus* by Hot-Soxlation Method

The coarse powdered material of tubers/rhizomes/roots of *Cyperus scariosus* was subjected to hot-soxlation using solvents n-hexane, dichloromethane, chloroform, ethyl acetate, acetone, ethanol, methanol, water, chloroform and methanol (1:1), methanol and water (1:1) and ethyl alcohol and water (1:1) at optimum temperature and recycled until extraction is completed, then plant extract were filtered and concentrated the filtered plant extract to dryness on rotatory evaporator or on steam bath at optimum temperature.

All extracts such as n-hexane extract (CS-1), dichloromethane extract (CS-2), chloroform extract (CS-3), ethyl acetate extract (CS-4), acetone extract (CS-5), ethanol extract (CS-6), methanol extract (CS-7), water extract (CS-8), choloroform:methanol (1:1) extract (CS-9), methanol:water (1:1) extract (CS-10) and ethanol:water (1:1) extract (CS-11) prepared from the tubers/roots/rhizomes of *Cyperus scariosus* by using percolation method or hot-soxlation method were subjected to HPTLC (High Performance Thin Layer Chromatography) and HPLC (High performance Liquid chromatography) in various mobile phases on precoated TLC plates (Merck) and ODS column for qualitative and quantitative estimation of marker compounds and active principles. It was found that the extracts CS-1 to CS-11 were qualitatively and quantitatively similar to each other.

EXAMPLE 5

Screening of Plant Extracts for HBsAg Suppression Activity

The extracts CR-1 to CR-11 and CS-1 to CS-11 were subjected to biological screening in PLC/PRF/5 cells for in vitro HBsAg suppression activity. These cells were maintained in DMEM supplemented with 10% Fetal Calf Serum (FCS) and antibiotics (100 IU/ml of penicillin and 100 μg/ml of streptomycin) till they achieved 80% confluence in a humidified atmosphere containing 5% $CO_2$ at 37° C. The cultures were massaged by trypsinization upon confluence on a regular basis.

The stock solutions of the plant extracts CR-1 to CR-11 and CS-1 to CS-11 (50 mg/ml) were prepared in Dimethyl Sulphoxide (DMSO) or in water as per the solvent specification. The working solutions of the plant extracts (10 mg/ml) were prepared in serum free Dulbecco's Modified Eagle's Medium (DMEM) and filter sterilized.

For assaying the effect of the extract on HBsAg expression, cells were seeded into a 96-well tissue culture plate at a density of $5 \times 10^4$ cells per well and incubated for 24 h. The cells were then washed twice with incomplete medium and incubated with various concentrations of extracts in serum-free DMEM for 24 h Culture supernatants were then collected and HBsAg in culture medium was measured by an ELISA system. The levels of HBsAg suppression in the treatment and in the control groups were recorded.

The results of HbsAg suppression activity of various extracts are summarized in Table-1

TABLE 1

| Extract | Suppression of HbsAg (%) | Extract | Suppression of HbsAg (%) |
|---|---|---|---|
| Control | 0.00 | Control | 0.00 |
| CR-1 | 0.00 | CS-1 | 0.00 |
| CR-2 | 0.00 | CS-2 | 0.00 |
| CR-3 | 0.00 | CS-3 | 0.00 |
| CR-4 | 0.00 | CS-4 | 0.00 |
| CR-5 | 20.50 | CS-5 | 16.50 |
| CR-6 | 90.08 | CS-6 | 79.50 |
| CR-7 | 94.19 | CS-7 | 85.35 |
| CR-8 | 20.90 | CS-8 | 24.50 |
| CR-9 | 17.80 | CS-9 | 16.25 |
| CR-10 | 12.50 | CS-10 | 14.50 |
| CR-11 | 32.14 | CS-11 | 28.74 |

Among all 22 extracts screened for the suppression of HBsAg activity, the methanol extract (CR-7), ethanol extract (CR-6) of *Cyperus rotundus* and the methanol extract (CS-7) and ethanol extract (CS-6) of *Cyperus scariosus* were shown promising activity. In order to study the detailed mechanism of action and efficacy of the extract in Hepatitis B patients, the most active extract i.e. CR-7 from *Cyperus rotundus* was taken up for further evaluation and hereafter CR-7 is recoded as CY-23.

EXAMPLE 6

Screening of CY-23 the Cell Models PLC/PRF/5 and HepG2.2.2.15 Cells

The plant extract CY-23 effectively suppressed the production of HBsAg in both the cell models studied namely, PLC/PRF/5 and HepG2.2.2.15 cells. CY-23 was able to suppress the surface antigen production in a dose dependent manner. A concentration of 200 μg/ml was found to be ideal for the extract to suppress the HBsAg production to the extent of 95% in PLC/PRF/5 cells and to the extent of 85% in Hep.G2.2.2.15 cells. The details on the level of suppression are presented in the table 2 and 3 below.

TABLE 2

| Concentration | Level of Suppression (%) | |
|---|---|---|
| (ug) | CY-23 | Control |
| 200 | 95 | 0 |
| 100 | 85 | 0 |

TABLE 3

| Concentration | Level of Suppression (%) | |
|---|---|---|
| (ug) | CY-23 | Control |
| 200 | 85 | 0 |
| 100 | 64 | 0 |

EXAMPLE 7

Bioassay Guided Fractionation of CY-23

The extract CY-23 is subjected to bioassay guided fractionation in to hexane soluble fraction (J-1), dichloromethane soluble fraction (J-2), ethyl acetate soluble fraction (J-3), methanol soluble fraction (J-4) and water-soluble fraction (J-5). All these fractions J-1 to J-5 subjected to HbsAg suppression activity on PLC/PRF/5 cell lines. The results are summarized in the table-4

TABLE 4

| Fraction No. | Suppression (%) |
|---|---|
| Control | 0 |
| J-1 | 0 |
| J-2 | 14 |
| J-3 | 98 |
| J-4 | 64 |
| J-5 | 13 |

EXAMPLE 8

Characterization and Purification of Active Fraction J-3

The active fraction J-3 subjected to HPTLC over precoated silica gel plates (Merck) and run in different mobile phases. The plates were air dried and sprayed with Anisaldehyde-Sulphuric acid reagent to visualize spots. Fraction J-3 also subjected to chemical identification tests using in house methods to identify the principle active compounds and markers. The fraction J-3 mainly comprises flavonoids, terpenoids, sesquiterpene lactones, anthraquinones, glycosidic compounds, procyanidins, bitters, tannins and fixed oil. The active fraction J-3 was subjected to column chromatography over silica gel and eluted with dichloromethane, ethyl acetate and methanol with increasing polarity to yield 8 semi purified fractions, J-6 to J-13. All these fractions (J-6 to J-13) were screened for HBsAg suppression activity in PLC/PRF/5 cell line at 100-ug/ml concentration and results are given in table-5.

TABLE 5

| Fraction No. | Suppression (%) |
|---|---|
| Control | 0 |
| J-6 | 1 |
| J-7 | 20 |
| J-8 | 84 |
| J-9 | 98 |
| J-10 | 74 |
| J-11 | 22 |
| J-12 | 13 |
| J-13 | 38 |

The most active fraction J-9 with 98% suppression activity was shown positive test for terpenoids, sesquiterpene lactones, coumarines, aurones, phenolics and their corresponding glycosides etc. The active fraction J-9 also subjected to HPLC for marker identification on ODS column in mobile phase of Solvent A (0.05% Orthophosphoric acid in Methanol) and Solvent B (0.05% Orthophosphoric acid in Water) and detected in PDA detector.

EXAMPLE 9

Chemical Identification of Active Marker Compounds in CY-23

The active extract CY-23 was subjected to various chemical test to identify marker compounds present in the extract. The identification of these marker compounds helps in standardization of the active extract for various biological test and clinical trial and commercial production of the drug. The main constituents of CY-23 are terpenoids, sesquiterpene lactones, anthraquinones, flavonoids, alkaloids, saponins, bitters, procyanidins, glycosidic compounds and fixed oils etc.

EXAMPLE 10

Down Regulation of Surface Antigen and Elimination of Hepatitis B Virus by Extract CY23

Infection by Hepatitis B Virus (HBV) frequently results in acute and chronic hepatitis and is also associated with a high risk of developing primary hepato-cellular carcinomas in humans. Although immunization against HBV has been effective in preventing chronic infections, effective drugs to eradicate HBV in chronic carriers are still not available, so an extended search is necessary for newer drugs. The species specificity in the infectivity of HBV makes it difficult to evaluate a putative anti-HBV agent using animal models.

Close resemblance of Duck Hepatitis B Virus (DHBV), with the human hepatitis B virus has made it possible to evaluate the efficacy of the anti-HBV agents in ducks infected with DHBV. Thus, Duck model studies are considered to be ideal for evaluating such effects. Further, cell culture systems provide an alternative to in vivo models and permit screening of large number of potential anti-HBV agents.

In the present study, surface antigen suppression and HBV virus elimination activities of herbal extract CY-23 were examined using two hepatitis B surface antigen (HBsAg) expressing human hepato-cellular carcinoma cell lines, PLC/PRF/5 and HepG2.2.215. Polymerase chain reaction (PCR) for study of amplification of DNA specific to HBV, Reverse transcriptase inhibition assay, immunomodulatory effects and Hepatoprotective ability against oxidative damage to hepatocytes were some of the other studies performed to evaluate the efficacy of the plant extract.

An effort was also made to isolate the Duck Hepatitis B Virus from the clinical samples received from the wild ducks. The efficacy of the plant extract to eliminate the DHBV was assessed in experimentally infected Pekin ducks in a duck model study.

EXAMPLE 11

Cell Viability Assay

After removal of the culture supernatants, MTT assay was performed to assess the viability of cells. In brief, 80 μl of serum free medium with 20 μl of MTT (5 mg/ml in phosphate buffered-saline) were added to each well and the plate was incubated at 37° C. for 4 h. Then, 100 μl of 10% sodium dodecyl sulfate (in 0.01 N HCl) was added and the plate was incubated again overnight at 37° C. in a 5% $CO_2$ incubator to solubilize the formazan crystals. The plates were read on a micro plate reader using a reference wavelength of 690 nm and a test wavelength of 540 nm.

EXAMPLE 12

Assay for HBsAg Binding Activity

Serial dilutions of the extracts were mixed with an equal volume of sera positive for HBsAg and the mixture was incubated for 2 h at 37° C. The mixture was then assayed directly for HBsAg using an ELISA kit.

EXAMPLE 13

HBV Virus Elimination

In this experiment the ability of the plant extracts to eliminate the HBV virus particles was examined. Hepatitis B virus transfected HepG2.2.2.15 cells were incubated with the plant extract prepared in serum free DMEM for 12 days at 37° C. in a humidified atmosphere containing 5% $CO_2$. The cells were given media change with or without the plant extract on every third day. On day 12, the cells were trypsinized and DNA was isolated. The viral DNA extraction was carried out by treating the cells with 200 μl of 5M guanidine-thiocyanate, 50 mM Tris HCl (pH 7.5), 10 mM EDTA, 0.3 M 2-mercaptoethanol and 2% SDS. The mixture was heated to 65° C. for 2 minutes and cooled. The nucleic acids were then phenol chloroform extracted. The extracts were treated with $1/10^{th}$ volume of 3 M sodium acetate and 2.5 volume of isopropanol and were incubated at −20° C. for 1 hour. The pellets were re-suspended in 1×TE (10 mM Tris, 0.1 mM EDTA, pH.8), treated with the Proteinase K (20 mg/ml) and RNAse (5 mg/ml) incubated for 1 hour at 37° C. The DNA was finally extracted by ethanol precipitation.

EXAMPLE 14

DNA-Specific HBV PCR

The DNA was amplified using primers (300ng), dNTPs (100 μM each), Taq polymerase (5 units) and MgCl2 (2.5 mM). The PCR program (MJ Research PTC-100, USA) included 1 cycle of 5 min at 94° C., 30 cycles of (30s at 94° C., 50s at 53° C. and 150s at 72° C.) and one cycle of 5 min. at 72° C. The primers were forward primer (5'-CTG TGG AGT TAC TCT CGT TTT TGC-3' (SEQ ID NO: 1)) and backward primer (5'-CTA ACA TTG AGA TTC CCG AGA TTG-3' (SEQ ID NO: 2)) as reported by Ying and others. The amplified product of 523 bp a fragment in the core gene of HBV genome was visualized by ethidium bromide (Sigma, U.S.A) staining on an agarose gel (2%) by electrophoresis and documented (Pharmacia Biotech, Image Master VDS).

EXAMPLE 15

RT Assay

Reverse transcriptase is an enzyme responsible for reverse transcription of viral DNA from RNA and thus help in the production of virion and the surface antigens. The plant extract was assessed for its ability to inhibit the RT activity. The procedure in brief involved incubation of the extracts directly with the RT and assess its ability to synthesize DNA from the dNTPs provided in the medium. The newly synthesized DNA was then conjugated with the help of DIG labeled complementary DNA strand and the intensity of color produced further to addition of substrate was measured with the help of an ELISA reader.

EXAMPLE 16

Immunomodulatory Effects

The immunomodulatory activity of Cy 23 was assessed in cell line models using mouse macrophage cells (RAW 264.7) and in mouse fibroblast cells (L929).

EXAMPLE 17

Assay for Immunostimulatory Effects

Mouse macrophage (RAW 264.7) cells were plated at a cell density of 1×105 cells/well in a 96 well micro titer plate. After 24 h of incubation they were treated with filtered extract (200 μg/ml), Lip polysaccharide (1 μg/ml) or media and incubated for a further period of 18-24 h. The supernatants as such or diluted ($1/10^{th}$ or $1/20^{th}$) were transferred to pre-incubated (24 hrs) L929 cells ($4\times10^4$ cells per well). Prior to addition of the supernatant the cells were sensitized with 50 μl of Actinomycin-D (0.33% prepared in DMEM). After 24 h of incubation, 20 μl of MTT (5 mg/ml) and 4 hour later 100 ul of SDS (10%) were added to dissolve the formosan granules to estimate the cell viability following the transfer of supernatant from the RAW cells. The viability of RAW 264.7 cells (an indicator of extract toxicity) was estimated by adding MTT after the transfer of its supernatant to L929 cells.

EXAMPLE 18

Nitric Oxide (NO) Estimation

Macrophages are part of immune system (innate immunity) which phagocytose the intruder organism and kill them by release of toxic Nitric Oxide (NO). In this experiment, the ability of the plant extract to stimulate the macrophages for NO production was measured as nitrite released from mouse macrophage cells. Mouse macrophage cells were plated in 96-well culture plates (1×10⁵ cells/well) and incubated for 24 h at 37° C. in a humidified atmosphere containing 5% CO2/95% air. The spent media from each well was aspirated and replenished with fresh media and further incubated for 48 h with desired concentration of extract in presence or in absence of Lip polysaccharide (LPS 1 ug/ml). NO production in the supernatant was measured by micro plate assay. Cell supernatant was mixed with an equal volume of the Griess reagent (1% sulfanilamide and 0.1% N-[napthyl]ethylenediamine dihydrochloride in 2.5% $H_3PO4$) at room temperature for 10 min. The absorbance at 540 nm was determined in a micro titer plate reader. Nitric oxide estimation was carried out using standard curve plotted against known quantity of sodium nitroprusside. Results presented are in µM concentration obtained from mean OD of triplicate wells of each group.

EXAMPLE 19

Hepatoprotective Effects of CY 23 (In Vitro)

The hepato-protective ability of Cy 23 against oxidative damage to the liver cells was evaluated in HepG2 cells. These cells were plated at a cell density of 50000 cells per well in a 96 well micro-titer plate in DMEM supplemented with 10% FCS and incubated for 24 hours in a humidified atmosphere containing 5% $CO_2$ and 95% air. The cells were then challenged with various concentrations of 10 mM TBH (Tertiary Butyl Hydro peroxide). The oxidative damages to the liver cells in presence and in the absence of Cy 23 were measured by MTT assay. The absorbance recorded at 540 nm was converted to the percent toxicity in each group.

EXAMPLE 20

Hepatoprotective Effects of Cy 23 (In Vivo)

The Hepatoprotective ability of the Cy 23 was studied in experimental animal model. The study was conducted Wister rats against the hepatotoxic agents like Carbon tetra chloride ($CCl_4$-ml/kg body weight), Thioacetamide (100 mg/kg b. wt) and paracetamol (2000 mg/kg b. wt). The animals were divided into three (3) groups viz. normal control, positive control and group treated with cy 23 for 7 days followed by single dose of hepato-toxic agent (n=6). The serum enzyme levels were estimated for assessment of protection offered by Cy 23. Other parameters relevant to the study were also estimated.

EXAMPLE 21

In Vivo Duck Model Study

Ducks are considered to be ideal animal model for screening and evaluating the efficacy of antiviral agents against DHBV, which has a close resemblance with the human hepatitis B virus. As such anti DHBV agent could also be equally putative in combating the hepatitis on account of hepatitis B virus in human beings.

EXAMPLE 22

Duck Hepatitis B Virus Isolation

In the present investigation, clinical samples of wild ducks were received from the various parts of Southern India. Samples were preserved under cold conditions till it is processed. The viral DNA extraction was carried out using 200 µl of homogenized sample treated with 0.75 ml of 5M guanidine-thiocyanate, 50 mM Tris HCl (pH 7.5), 10 mM EDTA, 0.3 M 2-mercaptoethanol and 2% SDS. The mixture was heated to 65° C. for 2 minutes and cooled. The nucleic acids were then phenol chloroform extracted. The extracts were treated with $\frac{1}{10}^{th}$ volume of 3 M Sodium acetate and 2.5 volume of isopropanol and were incubated at −20° C. for 1 hour. The pellets were re-suspended in 1× TE (10 mM Tris, 0.1 mM EDTA, pH.8), treated with the Proteinase K (20 mg/ml) and RNAse (5 mg/ml) incubated for 1 hour at 37° C. The cccDNA was finally extracted by ethanol precipitation and restrict digested with EcoRI.

EXAMPLE 23 cccDAN-Specific DHBV PCR

The Eco R1 digested cccDNA was amplified using primers, dNTPs (250 µM each), Taq polymerase and MgCl2 (2.5 mM). The PCR program (MJ Research PTC-100, USA) included 1 cycle of 5 min at 94° C., 30 cycles of (30s at 94° C., 50s at 53° C. and 150s at 72° C.) and one cycle of 5 min. at 72° C. The primers were forward primer 2771 (5'-GAA TCT GAT TTC CAA TA-3' (SEQ ID NO: 3)) and backward primer 1579 (5'-ACG GGT CTA CTA TTT TA-3' (SEQ ID NO: 4)). The amplified product of 1192 bp was visualized by ethidium bromide staining on an agarose gel (2%) by electrophoresis and documented. The positive samples were identified and were as used for experimentally infecting the ducks in future studies.

Experimental Induction of DHBV Infection in Pekin Ducks

This study was conducted to experimentally induce the DHBV infection in pekin ducks. Day old ducklings were infected with the DHBV virus isolated from the wild ducks earlier and the onset of viremia was confirmed by PCR amplification cccDNA fragment of viral genome from the liver biopsy samples collected from the birds.

Ten (10) day old pekin ducklings inducted from the Central Duck Breeding Farm Hesarghatta, Bangalore. India were divided into two groups of 5 each control and treatment respectively. The ducklings identified by leg bands birds received all the humane care and management practices as per standard rearing practices prescribed.

EXAMPLE 24

DHBV Inoculation, DNA Isolation and PCR

On Day 3, five ducks injected 200 ul of $1/1000^{th}$ dilution of the Duck hepatitis B virus (DHBV) isolated earlier from the wild ducks. On Day 15, the ducks were secured, anaesthetized and sacrificed by severing the jugular vein. The visceral organ liver was collected DNA was isolated. The DHBV specific viral DNA was amplified by PCR and viral specific DNA band was visualized and documented.

EXAMPLE 25

Antiviral properties of Cy 23

This study was conducted in Pekin ducks. Thirty-day-old pekin ducklings were inducted in this study. They were divided in to three groups v.i.z. control, positive control (DHBV infected) and treatment (DHBV infected plus Cy 23 administered) of ten (10) each. The control group received the oral doses of saline for 12 weeks where as the positive control group received a single injection of 200 ul of DHBV viral culture i.p. isolated from wild ducks earlier in our laboratory. Treatment group received a dose of virus as in the positive group followed by CY-23 orally at a dose of 250 mg/kg body weight daily for 12 weeks. Birds of all the groups were subjected for liver biopsy on Day 15 to confirm and demonstrate the presence of DHBV infection. At the end of 12 weeks ducks of all the groups were anaesthetized and sacrificed. The liver along with the other visceral organs was collected for various studies.

Results

Cell Viability

Cell viability assay conducted in the PLC/PRF5 and Hep.G2.2.15 cells indicated that the extract was not toxic to the cell lines at various concentrations tested. The cells resumed normal growth after re-plating them into fresh medium.

Assay for Interference

Assay for direct binding of HBsAg with the extract showed that the plant extract did not interfere with the enzyme immunoassay of HBsAg determination. Also, HBsAg was found to be less in lysates (in 1% Triton X-100) of the cells incubated with the extract as compared to lysates of control cells.

HBV Specific DNA PCR

Figure 1:
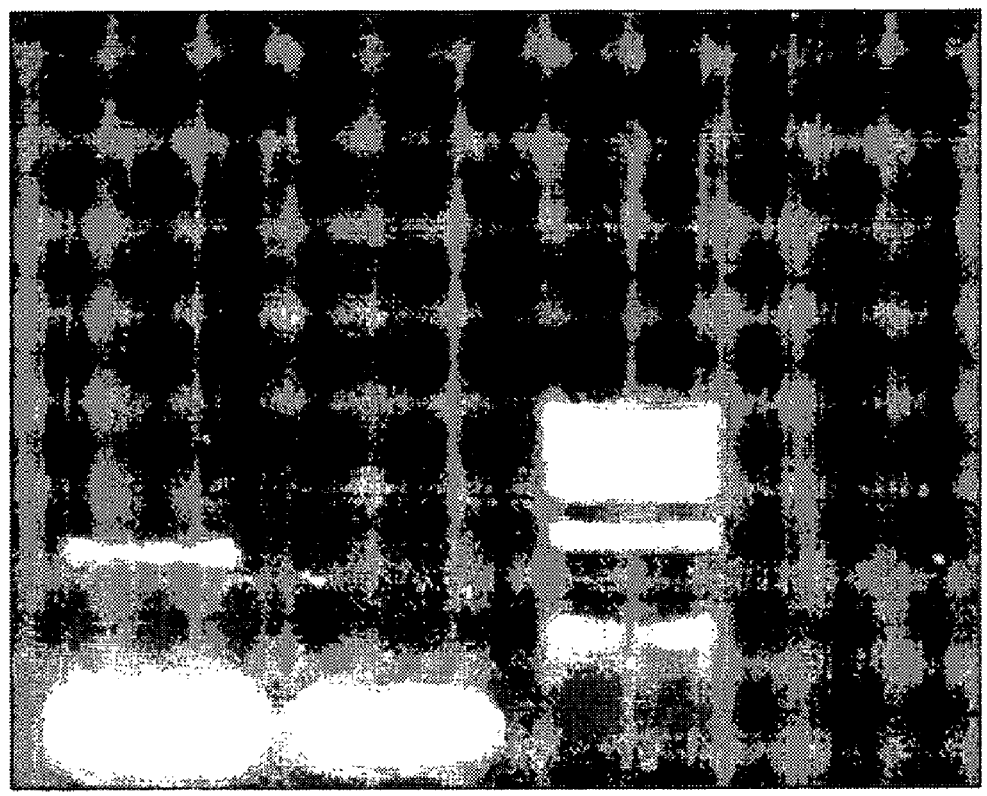
FIG. 1 HepG2.2.2.15 cells showing complete elimination of HBV specific DNA fragment following 12 days of incubation with CY 23

The polymerase chain reaction of the DNA extracted from the Hep.G2.2.15 cells continuously treated with the plant extract CY-23 for 12 days indicated the elimination of HBV viral particles from the treated hepatocytes. After 30 cycles of PCR, the treated group did not show amplification of the viral band however the control group showed amplification of a strong viral band (FIG. 1).

Assay for Immunostimulatory Effects

The assay conducted in the cell lines indicated that the supernatant of the macrophage cells were able to elucidate more than 50% death in the ACD sensitized L929 cells comparable to the levels in LPS group. The control group however did not exhibit the same level of damage. Further, MTT results of macrophage cells indicated that the plant extract was not toxic to the cells. Hence the death in L929 cells following the transfer of supernatant from RAW cells was not on account of plant extract toxicity but due to the cytokines released from the activated macrophages. The death of L929 cells indicates that the plant extract was able to stimulate the macrophage to produce the pro-inflammatory cytokines mainly TNF.

TABLE 6

| Groups | Survival (%) |
| --- | --- |
| Control | 100 |
| CY-23 | 49.33 |

Nitric Oxide (NO) Estimation

This experiment indicated that the macrophages were activated by the plant extract to produce nitric oxide to the levels comparable to LPS group, indicating that the plant extract was able to stimulate the innate immune system of the body and thus help preventing the invading organisms.

TABLE 7

| Groups | NO(μM) | NO(μM) |
| --- | --- | --- |
| Control | 2370.75 | 2291 |
| CY-23 | 3176.75 | 3233.5 |
| CY-23 + LPS | 3784.5 | 3654 |

Reverse Transcriptase Assay

The RT assay indicated that the extract was able to inhibit the reverse transcriptase activity to the extent of 63%.

TABLE 8

| Groups | Inhibition (%) |
| --- | --- |
| Positive | 0 |
| CY-23 | 63 |

Hepatoprotective Ability of CY-23

The experiment conducted in Hep.G2 cells revealed that the plant extract CY-23 was able to revere oxidative damage caused by TBH and offered complete protection to the hepatocytes. The death rate in the TBH treated group was 47.47% while addition of CY-23 to TBH completely protected the cells indicating its Hepatoprotective ability as in the group treated with CY-23 alone or the normal control.

TABLE 9

| Groups | Toxicity (%) | Survival (%) |
| --- | --- | --- |
| Control | Nil | 100 |
| TBH | 47.47 | 52.53 |
| CY-23 | Nil | 100 |
| CY-23 + TBH | Nil | 100 |

In Vivo Duck Model Study

DHBV Virus Isolation

The PCR amplification of DNA isolated from the liver homogenate samples showed amplification of DHBV specific viral genome in 7 samples illustrated in FIG. 2 and table-10 as below.

TABLE 10

| Number of Samples Screened | 54 |
| --- | --- |
| Samples showed PCR amplification | 07 |
| Samples showed No. amplification | 47 |

Experimental Induction of DHBV in Pekin Ducks

All the five ducklings which received the i.p injection of pooled DHBV expressing liver homogenate, showed the DHBV infection. This was confirmed by the PCR amplification of the DHBV specific viral genome in the DNA isolated from the liver cells 15 after the injection of infective dose (FIG. 3).

Antiviral Properties of CY-23

The antiviral property of CY-23 was assessed based on its ability to eliminate the viral particles from the concomitantly infected ducks. Ducklings challenged with DHBV on Day 3 and simultaneously administered with CY-23 orally at a dose of 250 mg/kg body weight daily for 12 weeks completely eliminated the virus from the infected birds. The birds were tested positive for DHBV infection on Day 15 by PCR for DHBV specific viral DNA amplification in liver biopsy samples (FIG. 4 & 5).

PLC/PRF/5 cells contain at least six hepatitis B viral genomes integrated into high-molecular-weight host DNA. But it produces and secretes only sAg and does not produce hepatitis B core Ag, the cryptic HBeAg or free virus particles[8]. HepG2/A2 is a clonal derivative of the human hepatoma cell line HepG2[6], which was transfected with tandemly arranged HBV DNA. The viral DNA has been integrated into a cellular chromosome and was stably maintained. These cell lines, considered a model for persistently HBV-infected livers[9] were used in the present study to evaluate the effect of these Hepatoprotective herbs in suppressing HBsAg expression in cell culture.

In this study, we have observed that the extract suppresses the production of HBsAg in two human hepatic carcinoma cells, PLC/PRF/5 and HepG2.2.15. The absence of cytotoxicity at the concentrations tested indicates that decrease in HBsAg is not due to adverse effect of the drug on cell viability. The extract itself was found not to interfere with the enzyme immunoassay of HBsAg estimation when incubated with HBsAg positive serum. Studies on cell lysates have detected comparatively lower amounts of HBsAg in the treated cells, suggesting that the extract did not block the secretion process of HBsAg from the cell membrane in the cell lines, but down-regulates the expression of the antigen.

Our investigation thus indicates that the extracts could reversibly inhibit cell growth and suppress HBsAg expression in both of the human hepato-cellular carcinoma cell line models. Since the above studies rule out the direct interaction of the substance with the antigen the mode of action of these hepato-protective herbs might be (a) direct suppression of promoter activity of HBsAg gene, or (b) blockage of the enhancer activity of viral enhancer I or II, or (c) direct destabilization of the viral RNA in the cells. Further, it can be hypothesized that the suppression of the HBsAg along with the elimination of HBV viral particles following the treatment with the extract is on account of the inhibition of reverse transcriptase activity.

The extract CY-23 was also found to be stimulating the immune system by way of macrophage activation, proinflammtory cytokine production and Nitric oxide production. These properties will possibly help in preventing the re-infection of hepatocytes by viral particles and help in eliminating the pathogen. The reversal of oxidative damage due to TBH in presence of CY 23 is an evidence of the Hepatoprotective ability of the plant extract.

All hepadnaviruses replicate their DNA genome through an mRNA intermediate the progenome RNA (pgRNA) by reverse transcription carried out by virally encoded reverse transcriptase (RT)). The understanding of hepatitis infection due to DHBV in ducks, which has structural similarity to HBV of humans, has made use of the duck as a suitable model to study human hepatitis B virus. Experimentally, DHBV has been useful in the study of molecular virology, pathogenesis and in the treatment of hepadnaviruses infection. Studies of DHBV infection in vitro and in Pekin ducks (*Anas domesticus*) have contributed significantly to the understanding of various aspects of the replication cycle of hepadnaviruses.

Process for preparation of Pharmaceutical Formulations comprising extract of plants *Cyperus rotundus* and/or *Cyperus scariosus* and pharmaceutically acceptable carriers to provide different delivery systems. The active extract CY-23 has been renamed as HD-03/ES for the study of pharmaceutical dosage forms and clinical trials in human beings.

EXAMPLE 26

Preparation of HD-03/ES Syrup

| Sl. No. | Name of Ingredient, | Formula I | Formula II | Formula III | Formula IV | Formula V |
|---|---|---|---|---|---|---|
| 1 | HD-03/ES - extract IH | 50 mg | 100 mg | 125 mg | 250 mg | 500 mg |
| 2 | Sugar D 30/IP | 3.4 gm | 3.4 gm | 3.4 gm | 3.5 gm | 3.75 gm |
| 3 | Citric acid IP | 0.01 mg | 0.01 mg | 0.01 mg | 0.02 mg | 0.02 mg |
| 4 | Methyl paraben sodium IP | 0.01 mg | 0.01 mg | 0.01 mg | 0.01 mg | 0.01 mg |
| 5 | Propyl paraben sodium IP | 0.0025 mg | 0.0025 mg | 0.0025 mg | 0.0025 mg | 0.0025 mg |
| 6 | Strawberry flavor IFF | 0.005 mg | 0.005 mg | 0.005 mg | 0.005 mg | 0.005 mg |
| 7 | DM water IP | Qs to 5 ml | Qs to 5 ml | Qs to 5 ml | Qs to 5 ml | Qs to 5 ml |

Process for Preparation:

First sugar was dissolved with DM Water in a jacketed vessel, then extract was added into the solution and mixed for 10-15 min. and the resultant was filtered through Polypropylene pad into another jacketed vessel, then citric acid was dissolved in small quantity of DM water and mixed with the resultant, methyl paraben sodium and propyl paraben sodium was dissolved in small quantity of DM water and mixed with the resultant mixture at 60° C.-70° C. and then the mixture was cooled, flavor was added at 40° C. or less and mixed for 5-10 min. Then the volume was maintained, and mixed for 10-15 min. and filtered to a clean storage vessel through Polypropylene pad (10 micron).

EXAMPLE 27

Preparation of HD-03/ES Tablets

| Sl No. | Name of Ingredient, | Formula I | Formula II | Formula III | Formula IV | Formula V | Formula VI |
|---|---|---|---|---|---|---|---|
| 1 | HD-03/ES extract IH | 50 mg | 100 mg | 150 mg | 200 mg | 250 mg | 500 mg |
| 2 | Microcrystalline cellulose IP | 450 mg | 350 mg | — | — | 100 mg | 100 mg |
| 3 | P. G. Starch IP | — | 50 mg | 50 mg | — | — | — |
| 4 | Lactose IP | — | — | 300 mg | 50 mg | 100 mg | 150 mg |

-continued

Preparation of HD-03/ES Tablets

| Sl No. | Name of Ingredient, | Formula I | Formula II | Formula III | Formula IV | Formula V | Formula VI |
|---|---|---|---|---|---|---|---|
| 5 | Dibasic calcium phosphate IP | — | — | — | 250 mg | 50 mg | 200 mg |
| 6 | DM water IH | Q.S. | Q.S. | Q.S. | Q.S. | Q.S. | Q.S. |

Process for Preparation:

Formula I: Microcrystalline cellulose IP (Passed through Sieve No. 60) was loaded in a suitable mixer and granulated with HD-03/ES extract IH and DM Water. The wet mass was passed through Sieve No. 8 and dried in suitable drier till the moisture content of 2-4%. The dried mass was passed through Sieve No. 16 and the lot was mixed uniformly.

Formula II: Microcrystalline cellulose IP and P. G. Starch IP (Both passed through Sieve No. 60) were loaded in a suitable mixer and mixed for 5 mins and granulated with HD-03/ES extract IH and DM Water. The wet mass was passed through Sieve No. 8 and dried in suitable drier till the moisture content of 2-4%. The dried mass passed through Sieve No. 16 and the lot was mixed uniformly.

Formula III: P. G. Starch IP and Lactose IP (Both passed through Sieve No. 60) were loaded in a suitable mixer and mixed for 5 mins and granulated with HD-03/ES extract IH and DM Water. The wet mass was passed through Sieve No. 8 and dried in suitable drier till the moisture content of 2-4%. The dried mass passed through Sieve No. 16 and the lot was mixed uniformly.

Formula IV: Lactose IP and Dibasic calcium phosphate IP (Both passed through Sieve No. 60) were loaded in a suitable mixer and mixed for 5 mins and granulated with HD-03/ES extract IH and DM Water. The wet mass was passed through Sieve No. 8 and dried in suitable drier till the moisture content of 2-4%. The dried mass passed through Sieve No. 16 and the lot was mixed uniformly.

Formula V: Microcrystalline cellulose IP, Lactose IP and Dibasic calcium phosphate IP (Both passed through Sieve No. 60) were loaded in a suitable mixer and mixed for 5 mins and granulated with HD-03/ES extract IH and DM Water. The wet mass was passed through Sieve No. 8 and dried in suitable drier till the moisture of 2-4%. The dried mass passed through Sieve No. 16 and lot was mixed uniformly.

Formula VI: Microcrystalline cellulose IP, Lactose IP and Dibasic calcium phosphate IP (Both passed through Sieve No. 60) were loaded in a suitable mixer and mixed for 5 mins and granulated with SL Noland DM Water. The wet mass was passed through Sieve No. 8 and dried in suitable drier till the moisture of 2-4%. The dried mass passed through Sieve No. 16 and lot was mixed uniformly.

Pharmaceutical ingredients for Tablet compression (Formula I to VI)

| Sl. No. | Name of Ingredient | Formula I to V Mg/Tablet | Formula VI Mg/Tablet |
|---|---|---|---|
| 1 | HD-03/ES granules IH | 500.00 | 950.00 |
| 2 | Sodium starch Glycolate IP | 30.00 | 30.00 |
| 3 | Calcium carbonate IP | 14.00 | 14.00 |
| 4 | Cabosil M5 IP/USP | 3.00 | 3.00 |
| 5 | Magnesium stearate IP | 3.00 | 3.00 |
| | Total | 550.00 | 1000.00 |

Procedure of Compression:

Sodium starch Glycolate IP, Calcium carbonate IP and Cabosil M5 IP/USP were mixed and passed through Sieve No. 60 and blended in a suitable mixer with HD-03/ES granules IH for 5 min., Magnesium stearate IP was passed through Sieve No. 60 and blended with the above for 3 min. The blend was ready for tablet compression.

Tooling: Caplet Shape, Round Shape, Oval Shape, and Triangular Shape etc.

EXAMPLE 28

Preparation of HD-03/ES Capsules

| Sl No. | Name of Ingredient, | Formula I | Formula II | Formula III | Formula IV | Formula V |
|---|---|---|---|---|---|---|
| 1 | HD-03/ES extract IH | 50 mg | 100 mg | 150 mg | 200 mg | 250 mg |
| 2 | Micro crystalline cellulose IP | 250 mg | 150 mg | — | — | 100 mg |
| 3 | P. G. Starch IP | — | 50 mg | 50 mg | — | — |
| 4 | Lactose IP | — | — | 300 mg | 50 mg | 100 mg |
| 5 | Dibasic calcium phosphate IP | — | — | — | 250 mg | 50 mg |
| 6 | DM water IH | Q.S. | Q.S. | Q.S. | Q.S. | Q.S. |

Process for Preparation:

Formula I: Microcrystalline cellulose IP (Passed through Sieve No. 60) was loaded in a suitable mixer and granulated with HD-03/ES extract IH and DM Water. The wet mass was passed through Sieve No. 8 and dried in suitable drier till the moisture content of 2-4%. The dried mass passed through Sieve No. 16 and lot was mixed uniformly.

Formula II: Microcrystalline cellulose IP and P. G. Starch IP (Both passed through Sieve No. 60) were loaded in a suitable mixer and mixed for 5 min. and granulated with HD-03/ES extract IH and DM Water. The wet mass was passed through Sieve No. 8 and dried in suitable drier till the moisture content of 2-4%. The dried mass was passed through Sieve No. 16 and mixed uniformly.

Formula III: P. G. Starch IP and Lactose IP (Both passed through Sieve No. 60) were loaded in a suitable mixer and mixed for 5 min. and granulated with HD-03/ES extract IH and DM Water. The wet mass was passed through Sieve No. 8 and dried in suitable drier till the moisture content of 2-4%. The dried mass was passed through Sieve No. 16 and mixed uniformly.

Formula IV: Lactose IP and Dibasic calcium phosphate IP (Both passed through Sieve No. 60) were loaded in a suitable mixer and mixed for 5 min. and granulated with HD-03/ES extract IH and DM Water. The wet mass passed through Sieve No. 8 and dried in suitable drier till the moisture content of 2-4%. The dried mass was passed through Sieve No. 16 and mixed uniformly.

Formula V: Microcrystalline cellulose IP, Lactose IP and Dibasic calcium phosphate IP (all passed through Sieve No. 60) were loaded in a suitable mixer and mixed for 5 min. and granulated with HD-03/ES extract IH and DM Water. The wet mass was passed through Sieve No. 8 and dried in suitable drier till the moisture content of 2-4%. The dried mass was passed through Sieve No. 16 and mixed uniformly.

| Capsule Filling Formula: | | | |
|---|---|---|---|
| Sl. No. | Name of Ingredient, | Formula I to II Mg/Capsule | Formula III to V Mg/Capsule |
| 1 | HD-03/ES granules IH | 300.00 | 500.00 |
| 2 | Cabosil M5 IP/USP | 2.00 | 2.00 |
| 3 | Magnesium stearate IP | 3.00 | 3.00 |
| | Total | 305.00 | 505.00 |

Description of capsule: Size '0' and '00' Clear transparent/or colored empty hard gelatine and/or Vegetable (HPMC) capsules.

Clinical trials of HD-03/ES in acute and chronic hepatitis B patients

A placebo controlled clinical study of the drug HD-03/ES was conducted in 50 patients suffering from acute and chronic hepatitis B for nine months during October 2003 and June 2004. 25 patients were treated with HD-03/ES (Two capsules twice a day) and other 25 patients received placebo. The results of clinical efficacy of the drug HD-03/ES including biochemical, immunological parameters are summarized in table 11 to table-14. A large-scale multicentric clinical trial of HD-03/ES is also under progress.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

TABLE 11

| | | Two-way RM ANOVA | | | | | | |
|---|---|---|---|---|---|---|---|---|
| Parameter | Source of Variation | % of total variation | Df | Sum-of-squares | Mean square | F | P value | P value summary |
| Appetite | Interaction | 8.7 | 5 | 13.75 | 2.749 | 16.6 | P < 0.0001 | Highly significant |
| | Score | 4.09 | 1 | 6.453 | 6.453 | 10.9 | 0.0018 | Significant |
| | Time | 44.05 | 5 | 69.56 | 13.91 | 84.1 | P < 0.0001 | Highly significant |
| | Subjects (matching) | 18.026 | 48 | 28.47 | 0.5931 | 3.59 | P < 0.0001 | Highly significant |
| | Residual | | 240 | 39.69 | 0.1654 | | | |
| Fatigue | Interaction | 3.57 | 5 | 6.747 | 1.349 | 8.25 | P < 0.0001 | Highly significant |
| | Score | 4.41 | 1 | 8.333 | 8.333 | 16.2 | 0.0002 | Highly significant |
| | Time | 58.2 | 5 | 110 | 22 | 135 | P < 0.0001 | Highly significant |
| | Subjects (matching) | 13.0511 | 48 | 24.67 | 0.5139 | 3.14 | P < 0.0001 | Highly significant |
| | Residual | | 240 | 39.25 | 0.1636 | | | |
| Weight loss | | 7.9 | 5 | 10.04 | 2.008 | 16.9 | P < 0.0001 | Highly significant |
| | | 2.36 | 1 | 3 | 3 | 5.06 | 0.0291 | Significant |
| | | 44.93 | 5 | 57.12 | 11.42 | 96.2 | P < 0.0001 | Highly significant |
| | | 22.3831 | 48 | 28.45 | 0.5928 | 4.99 | P < 0.0001 | Highly significant |
| | Matching by rows | | 240 | 28.51 | 0.1188 | | | |
| Jaundice | | 7.15 | 5 | 19.66 | 3.931 | 17.4 | P < 0.0001 | Highly significant |
| | | 7.57 | 1 | 20.8 | 20.8 | 15.2 | 0.0003 | Highly significant |
| | | 41.69 | 5 | 114.6 | 22.92 | 102 | P < 0.0001 | Highly significant |

TABLE 11-continued

Two-way RM ANOVA

| Parameter | Source of Variation | % of total variation | Df | Sum-of-squares | Mean square | F | P value | P value summary |
|---|---|---|---|---|---|---|---|---|
| | | 23.8666 | 48 | 65.61 | 1.367 | 6.05 | P < 0.0001 | Highly significant |
| | | | 240 | 54.23 | 0.2259 | | | |

TABLE 12

Serum Bilurubin
Two-way RM ANOVA

| Source of Variation | % of total variation | P value | P value summary | Df | Sum-of-squares | Mean square | F |
|---|---|---|---|---|---|---|---|
| Interaction | 17.52 | P < 0.0001 | Highly Significant | 2 | 649.7 | 324.9 | 31.07 |
| Concentration | 1.67 | 0.0445 | Significant | 1 | 61.81 | 61.81 | 4.26 |
| Time | 34.96 | P < 0.0001 | Highly Significant | 2 | 1297 | 648.3 | 62 |
| Subjects (matching) | 18.7808 | 0.0877 | Not Significant | 48 | 696.5 | 14.51 | 1.388 |
| Residual | | | | 96 | 1004 | 10.46 | |

Bonferroni post tests 0 vs. 16

| Concentration | 0 | 16 | Difference | 95% CI of diff. | t | P value | P value summary |
|---|---|---|---|---|---|---|---|
| Drug | 12.15 | 2.028 | −10.12 | −12.45 to −7.789 | 11.06 | P < 0.001 | Highly Significant |
| Placebo | 5.018 | 4.28 | −0.7376 | −3.066 to 1.591 | 0.8065 | P > 0.05 | Not Significant |

0 vs. 24

| Concentration | 0 | 24 | Difference | 95% CI of diff. | t | P value | Summary |
|---|---|---|---|---|---|---|---|
| Drug | 12.15 | 1.256 | −10.89 | −13.22 to −8.561 | 11.91 | P < 0.001 | Highly Significant |
| Placebo | 5.018 | 2.28 | −2.738 | −5.066 to −0.4093 | 2.993 | P < 0.01 | Significant |

TABLE 13

SGPT
Two-way RM ANOVA

| Source of Variation | % of total variation | P value | P value summary | Df | Sum-of-squares | Mean square | F |
|---|---|---|---|---|---|---|---|
| Interaction | 12.04 | P < 0.0001 | Highly Significant | 2 | 676200 | 338100 | 15.73 |
| Concentration | 0.97 | 0.152 | Highly Significant | 1 | 54420 | 54420 | 2.119 |
| Time | 28.29 | P < 0.0001 | Highly Significant | 2 | 1589000 | 794400 | 36.97 |
| Subjects (matching) | 21.9533 | 0.2282 | Highly Significant | 48 | 1233000 | 25680 | 1.195 |
| Residual | | | | 96 | 2063000 | 21490 | |

Bonferroni post tests 0 vs. 16

| Concentration | 0 | 16 | Difference | 95% CI of diff. | t | P value | P value summary |
|---|---|---|---|---|---|---|---|
| Drug | 440.2 | 119.6 | −320.6 | −426.2 to −215.1 | 7.733 | P < 0.001 | Highly Significant |
| Placebo | 212.6 | 187.4 | −25.2 | −130.7 to | 0.6078 | P > 0.05 | Not Significant |

TABLE 13-continued 80.35

0 vs. 24

| Concentration | 0 | 24 | Difference | 95% CI of diff. | t | P value | Summary |
|---|---|---|---|---|---|---|---|
| Drug | 440.2 | 58.4 | −381.8 | −487.3 to −276.3 | 9.208 | P < 0.001 | Highly Significant |
| Placebo | 212.6 | 103.8 | −108.8 | −214.4 to −3.294 | 2.625 | P < 0.05 | Significant |

TABLE 14

| | Serological parameters | | |
|---|---|---|---|
| Fisher's exact test | HBV DNA | HBe Ag | HBs Ag |
| P value | P < 0.0001 | 0.0005 | 0.0106 |
| P value summary | Highly Significant | Highly Significant | Significant |
| Relative Risk (RR) | 7.33 | 3.60 | 9.00 |
| 99% confidence interval of RR | 1.793 to 29.99 | 1.223 to 10.60 | 0.6575 to 123.2 |
| Odds ratio (OR) | 53.78 | 10.29 | 13.50 |
| 99% confidence interval of OR | 5.709 to 506.6 | 1.832 to 57.76 | 0.7882 to 231.2 |
| Sensitivity | 0.88 | 0.78 | 0.90 |
| 99% confidence interval of sensitivity | 0.6878 to 0.9745 | 0.5630 to 0.9254 | 0.5550 to 0.9975 |
| Specificity | 0.88 | 0.74 | 0.60 |
| 99% confidence interval of specificity | 0.6878 to 0.9745 | 0.5371 to 0.8889 | 0.4333 to 0.7514 |
| Positive Predictive Value (PPV) | 0.88 | 0.72 | 0.36 |
| 99% confidence interval of PPV | 0.6878 to 0.9745 | 0.5061 to 0.8793 | 0.1797 to 0.5748 |
| Negative Predictive Value (NPV) | 0.88 | 0.80 | 0.96 |
| 99% confidence interval of NPV | 0.6878 to 0.9745 | 0.5930 to 0.9317 | 0.7965 to 0.9990 |
| Likelihood Ratio | 7.33 | 3.02 | 2.25 |

What is claimed is:

1. A method of treating hepatitis-B comprising:
administering to a patient in need of treatment of Hepatitis B a composition consisting essentially of a therapeutically effective amount of a *Cyperus rotundus* extract and/or a *Cyperus scariosus* extract in a pharmaceutically acceptable carrier;
wherein said extract is obtained by extracting roots and/or rhizomes of *Cyperus rotundus*, and/or roots and/or rhizomes of *Cyperus scariosus* with an organic solvent selected from the group consisting of: ethyl alcohol, methanol, water or combinations thereof.

2. The method of claim 1, wherein the organic solvent consists of water and ethyl alcohol.

3. The method of claim 1, wherein the molar ratio of water: ethyl alcohol is 1:1.

4. The method of claim 1, wherein the organic solvent is methanol and/or ethyl alcohol.

5. The method of claim 1, wherein the composition consists essentially of a methanol extract of roots and/or rhizomes of *Cyperus rotundus*, and/or a methanol extract of roots and/or rhizomes of *Cyperus scariosus*.

6. The method of claim 1, wherein said extract contains: alkaloids, bitters, glycosidic compounds, tannins, fixed oils, procyanidins, anthraquinone glycosides, flavonoids, terpenoids, terpenoid glycosides and amino acids.

7. The method of claim 1, wherein the composition is in an oral dosage form.

8. The method of claim 1, wherein the composition is formulated into one or more forms selected from the group consisting of: a tablet, a capsule, a pill, a granule, a syrup, a powder, a concentrate, and a dry syrup.

9. The method of claim 1, wherein the composition is formulated into a syrup.

10. The method of claim 9, wherein the syrup consists essentially of the *Cyperus rotundus* extract and/or the *Cyperus scariosus* extract in a pharmaceutically acceptable carrier, wherein the extract is present in an amount of 50 mg to 500 mg, wherein the carrier consists of sucrose in an amount of 3.4 to 3.75 g, citric acid in an amount of 0.01 to 0.02 mg, methyl paraben sodium in an amount of 0.01 mg, propyl paraben sodium in an amount of 0.0025 mg, Strawberry flavor in an amount of 0.005 mg and demineralized water q.s., and wherein said extract and pharmaceutically acceptable carriers are present in said amounts per 5 ml of dosage form.

11. The method of claim 1, wherein the composition is formulated into of granules.

12. The method of claim 11, wherein the granules consist essentially of an the *Cyperus rotundus* extract and/or the *Cyperus scariosus* extract in a pharmaceutically acceptable carrier, wherein the extract is present in an amount of 50 to 500 mg, wherein the carrier consists of microcrystalline cellulose in an amount of 100 to 450 mg, pregelatinized Starch in an amount of about 50 mg, lactose in an amount of 50 to 300 mg, dibasic calcium phosphate in an amount of 50 to 250 mg, and demineralized water q.s., and wherein said extract and pharmaceutically acceptable carriers are present in said amounts per 300 to 900 mg of dosage form.

13. The method of claim 11, wherein the composition is formulated into of a tablet.

14. The method of claim 13, wherein the tablet consists essentially of 500 to 900 mg of the granules and a pharmaceutically acceptable carrier, wherein the carrier consists of: sodium starch glycolate in an amount of about 30 mg, calcium carbonate in an amount of about 14 mg, silicon dioxide in an amount of about 3 mg and magnesium stearate in an amount of about 3 mg.

15. The method of claim 11, wherein the composition is formulated into of a capsule.

16. The method according to claim 15, wherein the capsule consists essentially of 300 to 500 mg of the granules and a pharmaceutically acceptable carrier, wherein the carrier comprises silicon dioxide in an amount of about 2 mg and magnesium stearate in an amount of about 3 mg.

\* \* \* \* \*

UNITED STATES PATENT AND TRADEMARK OFFICE
CERTIFICATE OF CORRECTION

PATENT NO. : 8,080,264 B2
APPLICATION NO. : 12/820064
DATED : December 20, 2011
INVENTOR(S) : Shankar Kumar Mitra, Ekta Saxena and Mallikarjun Narayan Dixit It is certified that error appears in the above-identified patent and that said Letters Patent is hereby corrected as shown below:

Title Page (Item 73) Assignee, lines 1-2, Change "Dubai (IN)" to --Dubai (UAE)--.

Title Page (Item 56) Column 2 line 8, Under Other Publications, change "Heptaitis" to --Hepatitis--.

At Column 1 line 40, Change "hepatits" to --hepatitis--.

At Column 1 line 56, Change "Piccrorhiza" to --Picrorhiza--.

At Column 2 line 6, After "preparation" insert --.--.

At Column 2 line 64, After "itself" insert --.--.

At Column 6 line 12, Change "by" to --bp--.

At Column 6 line 12, Change "ccc DNA" to --cccDNA--.

At Column 6 line 15, Change "by" to --bp--.

At Column 6 line 17, Change "by" to --bp--.

At Column 6 line 21, Change "by" to --bp--.

At Column 6 line 43, Change "(Nambiyar," to --(Nambiar,--.

At Column 6 line 54, Change "antifibrile," to --antifebrile,--.

At Column 7 line 33, Change "choloroform" to --chloroform--.

At Column 8 line 10, Change "choloroform" to --chloroform--.

At Column 9 line 55, After "table-4" insert --.--.

At Column 13 line 10, Change "[napthyl]" to --[naphthyl]--.

Signed and Sealed this
Twelfth Day of June, 2012

David J. Kappos
*Director of the United States Patent and Trademark Office*

CERTIFICATE OF CORRECTION (continued)
U.S. Pat. No. 8,080,264 B2

At Column 14 line 14, Change "cccDAN" to --cccDNA--.

At Column 14 line 36, Change "Hesarghatta," to --Hesaraghatta,--.

At Column 17 lines 45-46, Change "proinflammtory" to --proinflammatory--.

At Column 19 line 63, Change "Noland" to --No. 1 and--.

At Columns 23-24 line 1 (Table 12), Change "Bilurubin" to --Bilirubin--.

At Column 28 line 25, In Claim 11, after "into" delete "of".

At Column 28 line 27, In Claim 12, after "of" delete "an".

At Column 28 line 38, In Claim 13, after "into" delete "of".

At Column 28 line 47, In Claim 15, after "into" delete "of".